(12) United States Patent
Baraket et al.

(10) Patent No.: US 7,213,444 B2
(45) Date of Patent: May 8, 2007

(54) OPTOACOUSTIC GAS SENSOR

(75) Inventors: Mourad Baraket, New York, NY (US);
Urs Gerber, Oberglatt (SE); Olivier Ruffiner, Winterthur (SE); Mauro Feltre, Hombrechtikon (SE)

(73) Assignee: Carthago International Solutions, Inc., New York, NY (US)

( * ) Notice: Subject to any disclaimer, the term of this patent is extended or adjusted under 35 U.S.C. 154(b) by 41 days.

(21) Appl. No.: 11/130,316

(22) Filed: May 16, 2005

(65) Prior Publication Data
US 2006/0254340 A1 Nov. 16, 2006

(51) Int. Cl.
*G01N 21/00* (2006.01)

(52) U.S. Cl. .................. 73/24.01; 250/344

(58) Field of Classification Search .......... 73/24.1, 73/24.2, 24.3, 587, 24.01, 24.02, 24.03; 356/437, 356/432; 250/339.13, 343, 345, 344, 346
See application file for complete search history.

(56) References Cited

U.S. PATENT DOCUMENTS 4,885,469 A * 12/1989 Yamagishi et al. ......... 250/345
5,677,534 A * 10/1997 Araya ......................... 250/345
5,933,245 A * 8/1999 Wood et al. ................. 356/437
6,006,585 A * 12/1999 Forster ....................... 73/24.01
2003/0112019 A1* 6/2003 Forster et al. ............. 324/633

* cited by examiner

*Primary Examiner*—Hezron Williams
*Assistant Examiner*—Ryan Christensen
(74) *Attorney, Agent, or Firm*—DLA Piper US LLP; R. Blake Johnston

(57) ABSTRACT

An optoacoustic sensor for detecting one or more target gases includes a body featuring halves containing measurement cells. Each measurement cell is in communication with a light source and a microphone as well as the ambient atmosphere. Evaluation and control electronics are in communication with the light sources and the microphones sequentially illuminate the first and second light sources so that a measurement signal due to optoacoustic pressure variations from a target gas is generated by the microphone of the illuminated or gas active cell and a compensation signal is generated by the microphone of the non-illuminated or gas inactive cell. The compensation signal is subtracted from the measurement signal by the evaluation and control electronics to provide a sensor output signal.

26 Claims, 7 Drawing Sheets

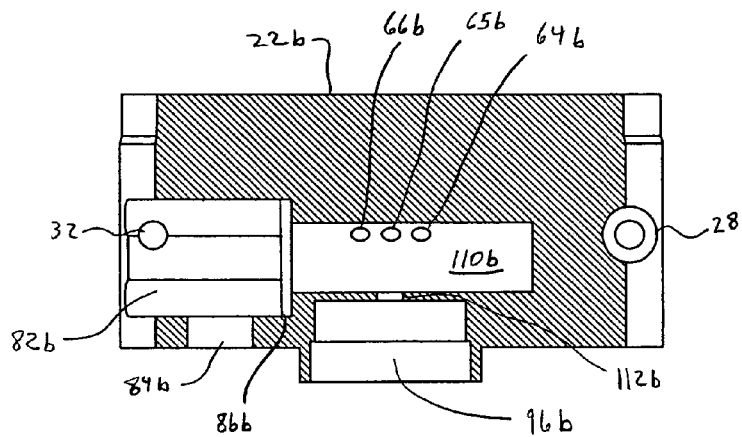
FIG. 6
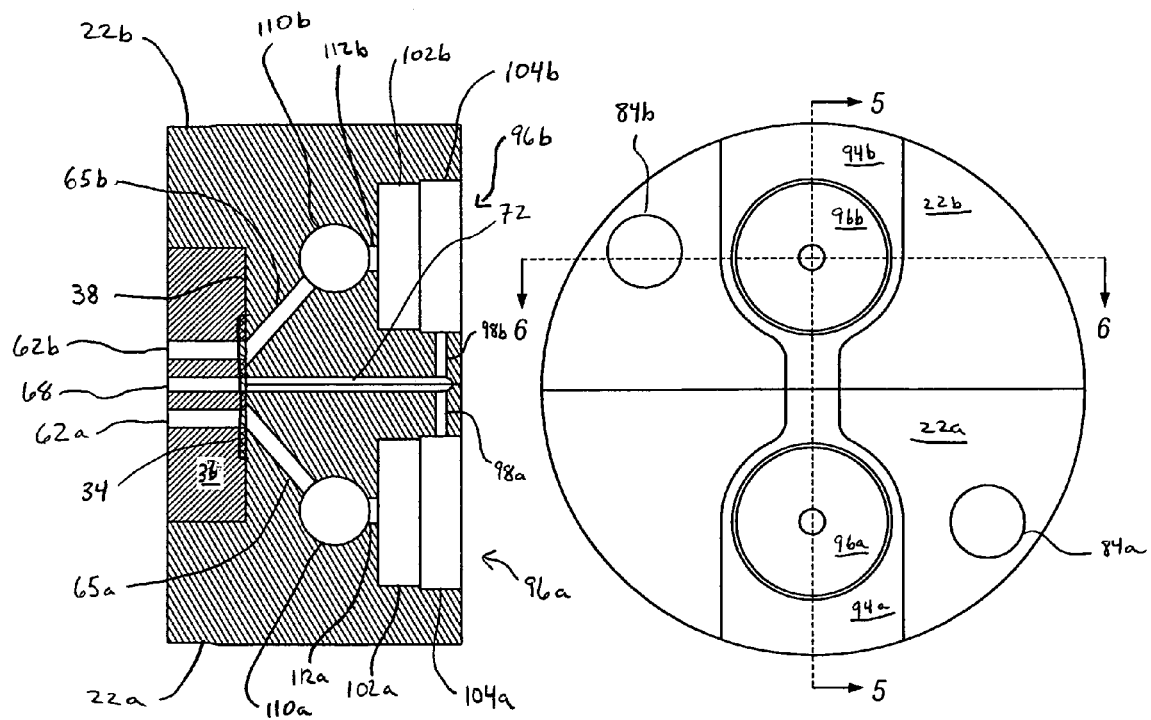
FIG. 5    FIG. 3

FIG. 7  Block Diagram of Sensor Circuit Borads

OPTOACOUSTIC GAS SENSOR

BACKGROUND OF THE INVENTION

The present invention generally relates to gas sensors and, more specifically, to an optoacoustic gas sensor.

Optoacoustic gas sensors have been used in various applications, including gas analyzers and gas detectors, to monitor environment gas concentration, most often for safety and process control purposes. Optoacoustic gas measurement is based on the same basic principles as conventional infrared-based gas analyzers—the ability of gases to absorb infrared light. More specifically, optoacoustic technology is based on generating acoustic pressure waves as result of gas irradiation with suitably modulated light.

A variety of optoacoustic gas sensors are known in the prior art. These include the optoacoustic gas sensors disclosed in U.S. Pat. No. 4,557,603 to Oehler et al.; U.S. Pat. No. 4,818,882 to Nexo et al.; U.S. Pat. No. 4,866,681 to Fertig; U.S. Pat. No. 5,753,797 to Forster et al.; U.S. Pat. No. 5,841,017 to Baraket et al. and U.S. Pat. No. 6,006,585 to Forster. These patents disclose arrangements where the sensor contains an infrared light source, a measurement cell, a membrane, a microphone and an electrical circuit for operating the light source and evaluating the microphone output signal. The light source transmits light pulses with specific wavelength into the measurement cell, where the radiation is absorbed by the gas to be detected and/or measured. Different gases can be measured by using light waves of different wavelengths corresponding to the absorption line of the gas to be measured. Therefore, the sensors may employ either narrow-band light sources, such as lasers, or wide-band light sources, such as incandescent filaments with optical band-pass filters.

When the gas to be detected is present in the environment within which the sensor is placed, the gas diffuses through the membrane into the measurement cell and there absorbs the light emitted. The absorbed radiation, which for very short time (a few microseconds) is stored as intermolecular vibrational-rotational energy, is quickly released by relaxation to translational energy during which numerous collisions occur between the gas molecules. Translational energy is equivalent to heat, which causes the pressure to rise in the absorption/measurement cell. If the incident light is modulated at a given frequency, a periodic pressure change is generated in the absorption cell.

At the edge of the measurement cell, the microphone captures the pressure modulation. The amplitude of the acoustic signal output is proportional to the radiation energy of the light source and the concentration of the absorbing gas. As a result, when the radiation energy is kept constant, the acoustic signal output can be measured and it delivers a value proportional to an absorbing concentration of gas.

There is quite frequently the need to detect and measure the concentration of multiple gases which are expected to be present or part of the process to be monitored. While it is possible to assign multiple sensors, each devoted to one specific gas, a single sensor distinctively measuring the concentration of multiple gases is undoubtedly a more economic alternative.

Furthermore, due to the nature of their detection principles, optoacoustic gas sensors have limited sensitivity. This is in part due to the effects of measurement cell wall effects, but is also due to environment pressure fluctuations and vibrations of several sources such as ventilation systems. It is therefore desirable to provide an optoacoustic gas sensor having a compensation cell in addition to the measurement cell that compensates for the interference signals generated exactly during gas measurement.

When it comes to reliability, the capability of gas sensors to have reliable self-diagnostic features to ensure the proper functionality of the sensor is undoubtedly most attractive. Most gas sensors do not have such capabilities. In addition, this capability must be technically feasible but also economically justifiable.

Gas sensors must be certified if they are to be installed in areas with intermittent or continuous presence of explosive gases (so-called "hazardous" or "classified" locations). To be certified, the design of a sensor must follow certain guidelines and fulfill strict requirements that are the subject of established standards. The most commonly applied standards for gas sensors relate to either explosion-proof or intrinsically safe design methods. It is therefore desirable to provide a sensor design that takes into consideration the most stringent certification requirements and fulfills either or both design methods.

Power consumption is becoming a crucial issue in the field of gas sensors as they are being increasingly used to detect and measure different gases from remote locations. Providing real-time measurements from distant locations puts a burden on sensors in terms of power consumption. It is therefore desirable to provide a gas sensor that features low power consumption.

It is also desirable to provide a gas sensor that corrects the effects of varying temperature so as to improve measurement accuracy.

It is also advantageous for the sensor output to represent not only the actual gas concentration, but also the gas concentration rate of increase, once a preset threshold has been reached or exceeded. For example, when a sensor is used to detect and measure natural gas (CH4) leaks, the rate of gas concentration increase may provide additional information regarding the severity of the leakage situation.

Accordingly, it is an object of the present invention to provide an optoacoustic gas sensor that can simultaneously measure the presence and concentration of multiple gases.

It is another object of the present invention to provide an optoacoustic gas sensor that compensates for interference signals.

It is another object of the present invention to provide an optoacoustic gas sensor that has reliable self-diagnostic features.

It is another object of the present invention to provide an optoacoustic gas sensor that may be certified as explosion-proof and/or intrinsically safe.

It is still another object of the present invention to provide an optoacoustic gas sensor that has low power consumption.

It is still another object of the present invention to provide an optoacoustic gas sensor that corrects for varying temperature.

These and other objects and advantages will be apparent from the following specification.

SUMMARY OF THE INVENTION

The present invention is directed to an optoacoustic gas sensor using two separate measurement and compensation cells that interchangeably act as a gas active measurement cell and a gas inactive compensation cell. The arrangement enables the sensor to measure two different gases simultaneously. If the sensor is dedicated to measuring one single gas, the compensation cell can be used as a redundancy measurement cell or as a measurement cell for an additional concentration range thereby extending the measurement concentration range of the overall sensor. The sensor incorporates a single membrane at the sensor inlet disposed such that it is equally divided between both cells. The overall sensor signal compensation is based on the non-irradiation of the compensation cell, making it completely gas-inactive during the actual compensation. The final measurement signal is the subtraction of the compensation cell signal from the measurement cell signal.

To compensate for the effect of pressure fluctuations, both cells feature a pressure balance drive connecting the rear side of both microphones with the atmosphere through a microphone compensation channel disposed at the interface of both sensor body halves. The monitoring of the light source intensity is achieved by keeping the power consumption of the infrared source constant. To monitor the proper functioning (functional condition) of the sensor microphones, the relationship between the outputs of both microphones is used. The output from the microphone of the measurement cell, i.e. the gas active cell, must equal or exceed the output of the microphone of the compensation cell, i.e. gas inactive cell, otherwise proper sensor function is not warranted.

The following detailed description of embodiments of the invention, taken in conjunction with the appended claims and accompanying drawings, provide a more complete understanding of the nature and scope of the invention.

BRIEF DESCRIPTION OF THE DRAWINGS

FIG. 3 is a bottom plan view of the assembled body halves of FIG. 2;

FIG. 5 is a sectional view of the sensor of FIG. 3 taken along line 5—5;

FIG. 6 is a sectional view of the sensor of FIG. 3 taken along line 6—6;

DESCRIPTION OF THE PREFERRED EMBODIMENTS

The subject invention is a gas sensor with a supplemental measurement cell primarily for compensation purposes. The supplemental measurement cell may be used to measure a second gas while not performing its primary compensation task and while the sensor primary cell measures a first gas. In addition, as explained below, the second measurement cell can be used as a redundancy cell, providing enhanced sensor reliability in case one of the cells fails to perform. The supplemental measurement cell may also act as range extending measurement cell, enhancing the sensor overall measurement range.

Figure 1:
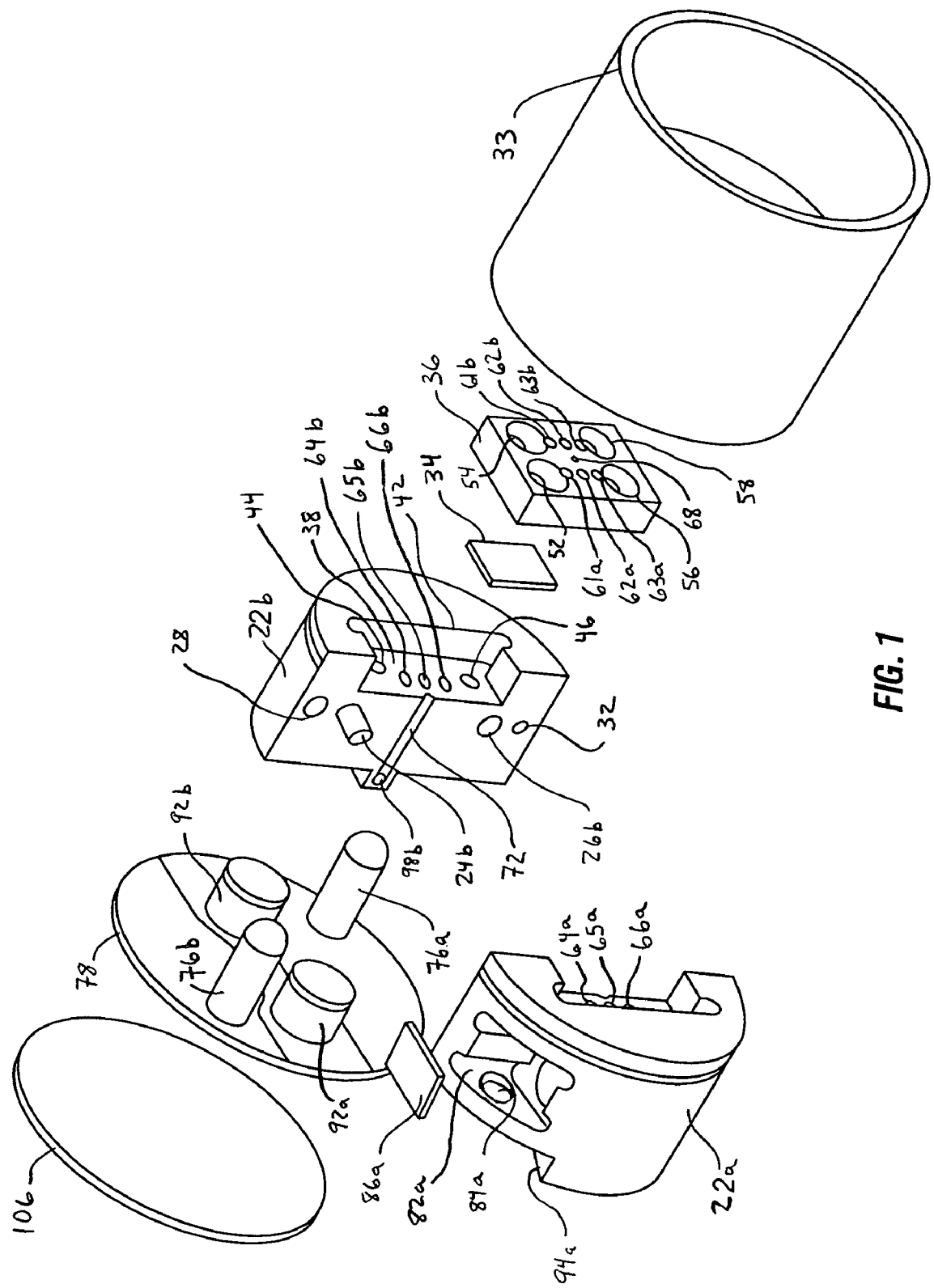
FIG. 1 is an exploded perspective view of an embodiment of the optoacoustic sensor of the present invention.
Figure 2:
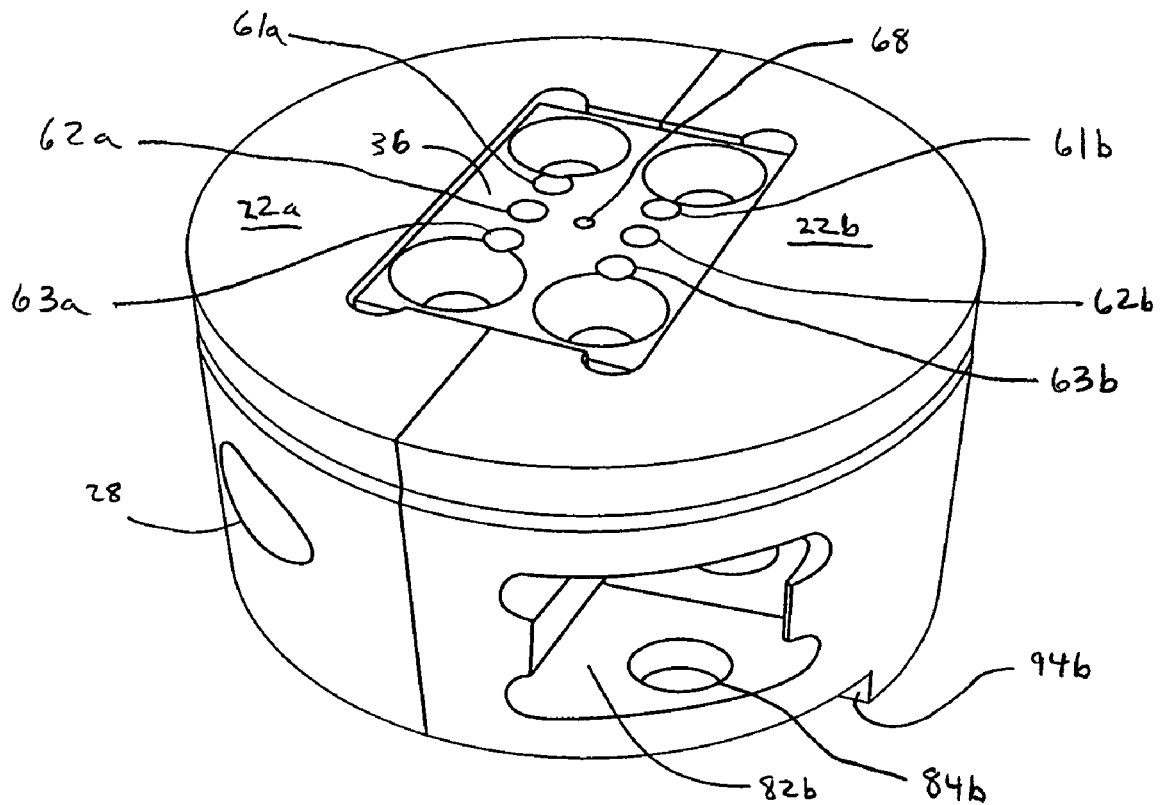
FIG. 2 is a perspective view of the assembled body halves and perforated plate of the sensor of FIG. 1.

As illustrated in FIG. 1, an embodiment of the optoacoustic gas sensor of the present invention features a cylindrical shape and contains two sensor body halves 22a and 22b. As shown for body half 22b in FIG. 1, and body half 22a in FIG. 4, each body half is provided with a positioning or adjustment pin 24b and 24a, respectively, and a positioning or adjustment bore 26b and 26a, respectively. The pin of one half engages the bore of the other half when the sensor body halves are assembled. A pair of screws (not shown) pass through holes 28 and 32 in body half 22b, and engage corresponding holes 29 and 31 (FIG. 4), respectively in body half 22a, to secure the two halves together as illustrated in FIG. 2. Once assembled, the sensor body halves are encapsulated in a cover tube 33 (FIG. 1), acting as additional holder of both sensor body halves. Body halves 22a and 22b and tube 33 preferably are constructed from stainless steel or aluminum.

As illustrated in FIG. 1, a membrane 34 is disposed under a perforated plate 36 that holds the membrane tight against the flat bottom 38 of a recess 42 formed in the top surface of the assembled sensor body by means of four screws (not shown) that engage holes 44 and 46 on body half 22b, corresponding holes on body half 22a, and holes 52, 54, 56 and 58 of plate 36 (see also FIG. 2). The plate is preferably approximately four mm thick to provide the mechanical stability required to guarantee that the membrane 34 does not vibrate, which would generate interference signals. It is also preferable that 38 be a plane surface as this enables the pressure over the entire membrane surface to be equally uniform, thus avoiding possible membrane vibrations and interference signals.

The plate 36 preferably includes holes 61a–63a and 61b–63b that communicate with the gas drives 64a–66a and 64b–66b of body halves 22a and 22b, respectively. As will be explained in greater detail below, the gas drives connect the measurement and compensation cells of the sensor to the atmosphere. In the middle of the perforated plate 36, an additional bore 68 is set to connect the microphone compensation channel 72 of the assembled sensor body, which will also be explained in greater detail below, with the atmosphere.

The light sources 76a and 76b are mounted on the sensor circuit board 78, which is part of the sensor evaluation and control electronics, before being inserted into the lamp chambers 82a (FIG. 1) and 82b (FIG. 2) through openings 84a and 84b, respectively. The infrared light sources may be either narrow-band light sources, such as lasers, or wideband light sources, such as incandescent filaments or light emitting diodes (LED). In the latter case, the optical bandpass filters 86a (FIG. 1) and 86b (FIG. 6) are required and feature absorption wavelengths corresponding to the target gases to measured.

As illustrated in FIG. 1, each lamp chamber is sandwiched between an optical bandpass filter 86a (if required) and sensor body tube 33. As a result, sensor body tube 33 seals the lamp chambers on their lateral surfaces and acts as a reflector, basically closing the lamp chambers and reflecting the emitted light through the bandpass filters. The optical bandpass filters 86a and 86b are preferably secured by means of adhesives in the lamp chambers.

As shown in FIG. 1, a pair of microphones 92a and 92b, which are used for detecting pressure waves in the measurement and compensation cells of the sensor, are mounted on the sensor circuit board 78. As illustrated FIGS. 1–3, the bottom surface of each body half is equipped with a raised portion 94a and 94b which house microphone holding chambers, illustrated at 96a and 96b in FIG. 3. When the sensor is assembled, the sensor circuit board 78 of FIG. 1 is positioned so as to abut the raised portions 94a and 94b on the bottom surface of the assembled sensor body and be circumferentially surrounded by cover tube 33. When the sensor circuit board is so positioned, the microphones 92a and 92b are positioned within the microphone holding chambers 96a and 96b of FIG. 3 and, as explained previously, lamps 76a and 76b (FIG. 1) are positioned within the lamp chambers 82a (FIG. 1) and 82b (FIG. 2).

Figure 4:
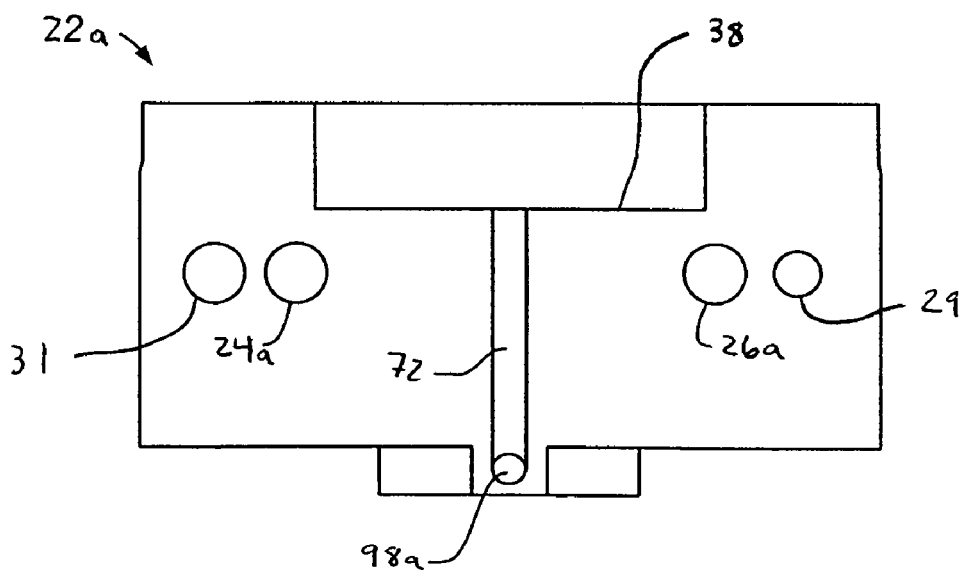
FIG. 4 is a side elevational view of the one of the body halves of the sensor of FIG. 1.

A microphone compensation channel, illustrated at 72 in FIGS. 1 and 4, is formed by the assembled body halves 22a and 22b and, as explained above, terminates in a top opening that communicates with bore 68 of the perforated plate 36, shown in FIGS. 1 and 2. As illustrated in FIG. 5, the bottom end of the microphone compensation channel 72 communicates with branches 98a and 98b which lead to the microphone holding chambers, indicated in general at 96a and 96b.

As illustrated in FIG. 5, each microphone holding chamber 96a and 96b includes an active portion 102a and 102b and a compensation portion 104a and 104b. The compensation portions 104a and 104b feature slightly larger diameters than the active portions 102a and 102b and communicate with branches 98a and 98b. The undersides of the microphones also communicate with compensation portions 104a and 104b. As a result, the undersides of the microphones are surrounded by spaces having a pressure that is equal with the pressure of the ambient atmosphere via the communication provided by microphone compensation channel 72, branches 98a and 98b and bore 68 of plate 36.

The circuit board 78 preferably is attached to raised portions 94a and 94b of the assembled sensor body with adhesive so as to form a seal between circuit board 78 and microphone holding chambers 96a and 96b. During assembly of the sensor, special care is required so that the microphone has no direct contact with the assembled sensor body itself. In addition, the adhesives used should not reach the bores formed in the microphone housing on the microphone active side. If the adhesive were to reach the bores, it could penetrate the microphone and damage the microphone membrane which would lead to the microphone loosing its sensitivity completely. Also care is required so that the adhesive does not stuff the crucial drive on the underside of the microphone housing that communicates with the compensation portion 104a or 104b of the microphone compensation chamber.

The mounting of the microphones on the sensor circuit board 78 rather than on the assembled sensor body, enables a critical manufacturing/quality advantage. More specifically, such an arrangement enables the functionality of the microphones to be tested before the circuit board 78 is incorporated into the sensor body by means of adhesives. Any corrective actions (e.g. change the microphone pairs) once the circuit board 78 is mounted, is complex, expensive and may lead to damaging the circuit board.

A second circuit board indicated at 106 in FIG. 1, which is also part of the sensor evaluation and control electronics, features a detector circuit and is connected to the first circuit board 78, before the assembled sensor body is inserted into the sensor body tube 33. Adhesives are also used to seal the assembled sensor body to the tube 33 and both circuit boards (78 and 106) on the inner side of the tube 33.

As illustrated in FIGS. 5 and 6, each body half 22a and 22b houses a cylindrical measurement and compensation cell 110a and 110b. As will be explained in greater detail below, each cell serves as a compensation cell when the remaining cell is serving as a measurement cell.

As illustrated in FIGS. 5 and 1, cell 110a communicates with the ambient atmosphere through gas drives 64a–66a, membrane 34 and holes 61a–63b of plate 36. Similarly, as shown in FIGS. 6, 5 and 1, cell 110b communicates with the ambient atmosphere through gas drives 64b–66b, membrane 34 and holes 61b–63b of perforated plate 36. As illustrated in FIG. 5, cells 110a and 110b communicate with microphone holding chambers 96a and 96b via acoustic passages 112a and 112b. As shown in FIG. 6, cell 110b communicates with lamp chamber 82b through bandpass filter 86b. Cell 110a of FIG. 5 communicates with lamp chamber 82a of FIG. 1 through bandpass filter 86a of FIG. 1.

The sensor of the present invention in one embodiment may operate as a two-gas optoacoustic sensor for the simultaneous detection and measurement of two different gases, for example carbon dioxide and methane. In operation, gases from the ambient atmosphere enter the sensor through holes 61a–63a and 61b–63b of plate 36 of FIGS. 1 and 2 and are diffused through the membrane 34. The diffused gases then travel through gas drives 64a–66a and 64b–66b into the measurement cells 110a and 110b.

The sensor infrared light sources 76a and 76b of FIG. 1 transmit light pulses through filters 86a and 86b with specific wavelengths into the measurement cells 110a and 110b. If the gases to be detected are present in cells 110a and 10b, the radiation is absorbed. The absorbed radiation causes the pressure to rise in the measurement cells 110a and 110b with a frequency that corresponds to the frequency of the incident light from light sources 76a and 76b.

The microphones 92a and 92b (FIG. 1), positioned in microphone holding chambers 96a and 96b of FIG. 5, capture the pressure modulation through acoustic passages 112a and 112b of FIG. 5. The radiation energy from the pulsating light sources 76a and 76b is kept constant so that the amplitude of the acoustic signal output is proportional to the concentration of the absorbing gas.

Figure 7:
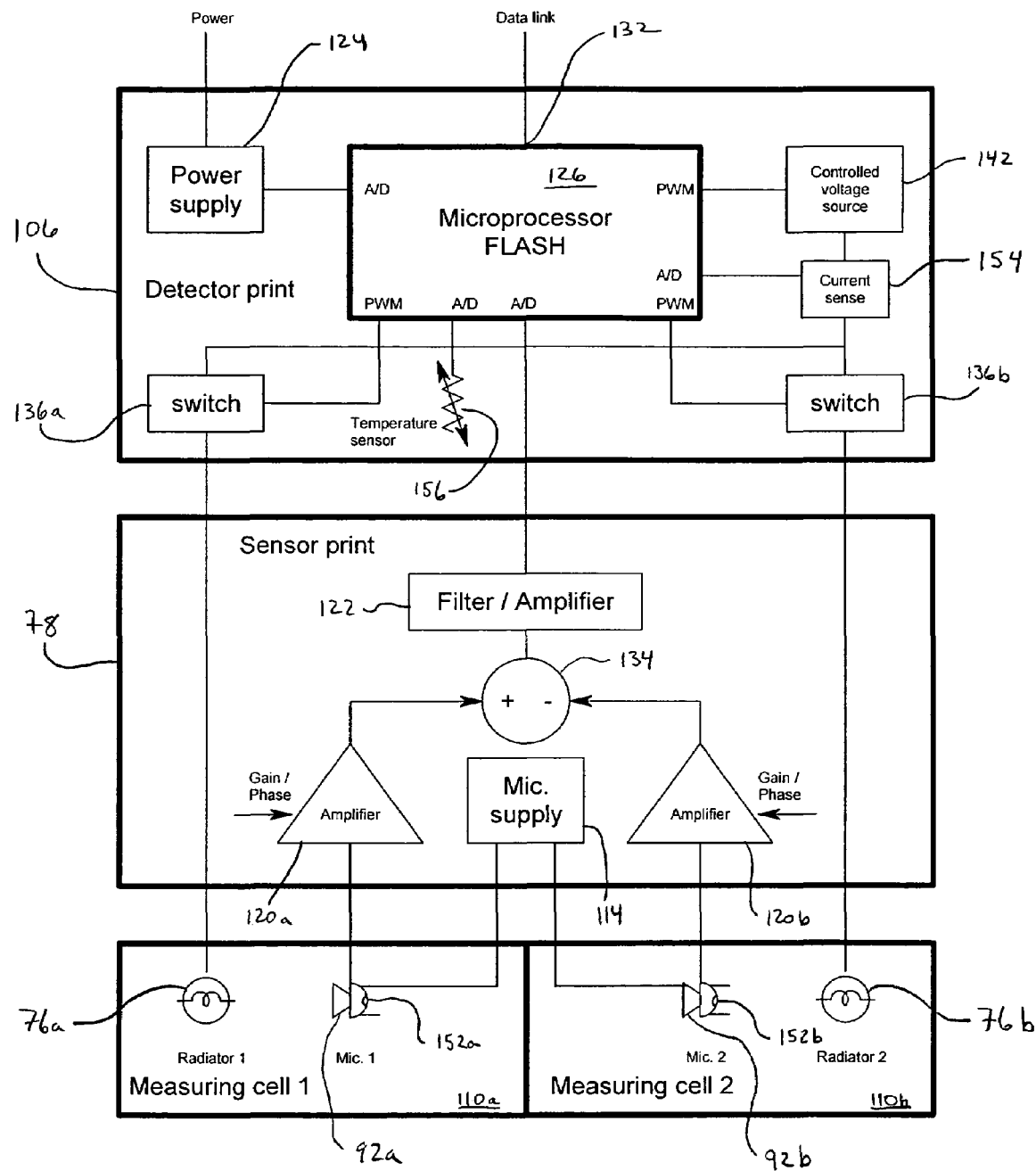
FIG. 7 is a block diagram of the circuit boards of the sensor evaluation and control electronics and the measurement and compensation cells of the sensor of FIG. 1.

The sensor evaluation and control electronics, including the two circuit boards 78 and 106 of FIGS. 1 and 7, power the sensor and evaluate both microphone signals. As illustrated in FIG. 7, circuit board 78 includes a power supply 114 for the microphones, microphone amplifiers 120a and 120b and a bandpass filter 122 tuned for the operation frequency.

Circuit board 106 contains a microprocessor power supply 124 and a microprocessor 126. The microprocessor preferably contains several 10-bit A/D (analog to digital) transformers, a serial data interface, PWM (pulse-width modulation) outputs and a programming interface. The operating program and parameters are preferably stored in a Flash memory and the measurement data are processed in the RAM (random access memory) of the microprocessor. During initial operation, the difference between both microphone signals is calibrated to a minimum so to improve the noise suppression.

With reference to FIG. 7, the pressure modulations generated in measurement cells 110a and 110b are converted by the microphones 92a and 92b into electrical signals. The electrical signals are amplified and filtered by amplifiers and filter 120a, 120b and 122 and the resulting signals are provided to microprocessor 126. Calibration values with which gas concentration levels are associated are stored in microprocessor 126 and the signals received by the microprocessor from circuit board 78 are compared with these calibration values to determine the gas concentration level detected by the sensors. Once a certain threshold, preset concentration level is reached, the sensor delivers a reading of the actual gas concentration as well as the rate of increase through data link port 132 of the microprocessor to a user display (not shown).

It should be noted that the rate of increase is an additional indication/information describing the dynamic process taking place around the sensor, and may be invaluable in some applications, especially those requiring higher safety standards.

The sensor operates in a sequential mode. For example, during a first sequence, measurement cell 110a is being irradiated via illuminated light source 76a, and thus is gas active measuring a first gas, while measurement cell 110b is not being irradiated, that is, light source 76b is not illuminated, and thus is gas inactive, even though microphone 92b is active. The second sequence is the opposite of the first sequence, that is, measurement cell 110b is being irradiated and thus is the gas active cell measuring the second gas and measurement cell 110a is completely gas inactive. As a result, during the first sequence, cell 110a acts as a measurement cell and cell 10b acts as a compensation cell while during the second sequence, cell 10a acts as a compensation cell and cell 110b acts as a measurement cell.

The compensation of deceptive signals is achieved by subtracting the compensation signal (from the gas inactive compensation cell) from the measurement signal (from the gas active measurement cell). The sensor signal output for the first gas is the subtraction of the signal of microphone 92b from the signal of microphone 92a, and the sensor signal output for the second gas is the subtraction of the signal of microphone 92a from the signal of microphone 92b, which takes place in circuit 134 of FIG. 7.

Activation of the light sources 76a and 76b of FIG. 7 is controlled by switches 136a and 136b and power to the lights is provided by voltage source 142. The frequency of the incident light from light sources 76a and 76b preferably is set at 23 Hz, which represents the upper frequency limit of the lamps but still within the band width of the microphones. During the switch from activation of lamp 76a to activation of lamp 76b, and vice versa, a measurement pause preferably of 480 ms takes place so that the filaments of the lamps cool down sufficiently between activations. As a result, the measurement sequence preferably takes place in the following sequences: 5 seconds measurement with measurement cell 110a active (and cell 110b acting as the compensation cell), 480 ms pause, 5 seconds measurement with measurement cell 110b active (and cell 10a acting as the compensation cell), 480 ms pause, and so on.

During the same pause of 480 ms, the deactivated lamp initiates a soft warm-up start through a pulse width modulation. Hereby the lamp is pulsed at a high frequency of about 100 KHz with a duty cycle of about 1%, gradually increasing to 100%. A major advantage of the gradual activation of the lamps is to extend the lifetime of the lamps and reduce the in-rush current by up to 70%, thereby contributing to the low power characteristic of the entire sensor.

In addition, during this measurement pause of 480 ms, both microphones are deactivated; i.e. the microphone signals are being ignored by the microprocessor. Indeed, interference noises caused by the gradual activation of a lamp may be detected by the microphone, thus it could generate a false reading.

The sequential operation of the sensor enables it to compensate the effect of ambient noises, pressure fluctuations and vibrations which can be captured by both microphones and otherwise would generate false output signals. The method described above also enables the sensor to offset inherent interference signals generated by the sensor itself as part of the overall background signal, thus increasing the sensor sensitivity.

Besides the need to have one measurement cell completely gas inactive during compensation, the choice of both microphones is crucial to effective compensation. More specifically, the microphone pair must show identical signal output as a precondition for accurate compensation in both measurement/compensation cells.

As an alternative to measuring two different gases, the sensor of the present invention may be configured to provide redundant functionality. In such an embodiment, both measurement cells are devoted to the same target gas in the same measurement range. The secondary measurement cell (cell 110b, for example) provides a redundant measurement to the primary measurement cell (cell 110a). Still measurement cell 110b in the gas-inactive mode would compensate for measurement cell 110a and vise versa.

In the event of a failure of the primary measurement cell, for example through failure of the infrared light source, the secondary measurement cell, basically a backup cell, would ensure the functionality of the sensor. The redundancy functionality provides higher system availability and control reliability at a very economical cost. This is especially useful in critical control applications that require maximum system availability.

Furthermore, in still another embodiment, the gas sensor can be used to measure the same gas in two different concentration ranges. For example, measurement cell 110a could be dedicated to gas concentrations in the lower range, for example 0 to 5% methane by volume, and measurement cell 110b could be dedicated to a higher concentration range, for example 5 to 100% methane by volume. As a result, the overall sensor measurement range can be as low as a few parts per million and as high as 100% methane by volume. Of course the compensation functionality also would still be operational in such an embodiment.

In such an embodiment measurement cells 110a and 110b have the same configuration with the exception that the volume (length) of measurement cell 110a is higher than the volume (length) of measurement cell 110b. The same effect can also be achieved by using light sources emitting two different radiation energies attributed to two identical measurement cells.

In summary, having an additional measurement and compensation cell not only achieves a reliable compensation function but also permits use of the additional cell in the gas active operation mode to measure an additional gas, to measure the same target gas in the same concentration range providing a redundancy function or to measure the same target gas in another concentration range leading to the extension of the sensor overall measurement range.

Each microphone 92a and 92b of FIG. 7 features an opening on its rear side, indicated at 152a and 152b. The opening is intended to provide a pressure balance or equalizing function as otherwise external pressure fluctuations may cause the microphone membrane to be damaged. Furthermore, as will be explained in greater detail below, the microphone back opening has a crucial compensation purpose.

The size of the microphone back opening is an important parameter. More specifically, the larger the size of the opening, the higher is the microphone's lowest measurable frequency limit. This means that if the microphone opening is too large, the microphone would be insensitive to low frequencies (for example 5 to 25 Hz) which happens to be the target operation frequency range of the microphone in the sensor. On the other hand, if the microphone opening is made too small, in order to decrease the microphone lowest measurable frequency limit (for example to 1 Hz), the microphone would be oversensitive to external frequencies in the sensor measurement range (5 to 25 Hz). Overreacting systems generate dead times which cannot be compensated for, or can even damage the microphone membrane. The preferred diameter of the openings 152a and 152b is 2 mm each.

In order for the sensor to compensate for external frequencies, either in the sensor measurement frequency range (e.g. 5 to 25 Hz) or in the low frequency range (e.g. 1 Hz), the microphone pressure balance must be guided through a channel with the same characteristics as the sensor gas measurement channels (64a–66a and 64b–66b of FIGS. 5 and 6). This is accomplished by placing the microphone back openings in communication with the compensation portions 104a and 104b of microphone holding chambers 96a and 96b which communicate with microphone compensation channel 72. As described previously, channel 72 communicates with the ambient atmosphere through membrane 34 and bore 68 of the perforated plate 36 of FIGS. 1 and 5.

Environment frequencies in the measurement frequency range are "absorbed" by the sensor membrane 34 (FIGS. 1 and 5) so that they do not reach the measurement cells nor the microphone holding chambers. Low frequencies, however, penetrate equally into the measurement cells and the microphone holding chambers but are compensated for via the microphone compensation function described previously.

The functionality diagnosis of both microphones is controlled by the microprocessor 126 of FIG. 7 continuously monitoring the output signals of both microphones. The signal output of the microphone associated with the gas active measurement cell must be of equal or higher value than the signal output of the microphone associated with the gas inactive compensation cell. If this condition is not fulfilled, then one or both microphones must be defective. In this case, a signal is generated by microprocessor 126 indicating microphone/sensor fault.

Photodiodes and infrared detectors are typically used to monitor the intensity of light sources in gas sensors. While photodiodes or silicon detectors show good stability, they can capture visible light only up to the near-infrared range. Capture of the spectrum of interest, i.e. 3 to 4.5 um, however, is not guaranteed. On the other hand, infrared detectors for the subject range of 3 to 4.5 um, e.g. mercury, cadmium, telluride or platinum silicide, show low stability at room temperature and, in addition, are highly dependent on temperature. Another option for monitoring the intensity of light sources is the use of thermopiles. Thermopiles have a slow reaction time, however, and as infrared detectors do not represent an economically attractive alternative.

Instead of the above options, the monitoring and control of the intensity of the light sources in the gas sensor of the present invention preferably is achieved by the microprocessor 126 of FIG. 7. The microprocessor constantly measures the lamp current I with current sensor 154 and voltage V from voltage source 142 and adjusts the lamp voltage as necessary so that the power consumption ($P = V \times I$) is held constant.

To compensate for the effects of temperature changes, the temperature of the target gas is measured by a temperature sensor, illustrated at 156 in FIG. 7, incorporated into the sensor circuit board 106. The temperature reading is used by the sensor microprocessor 126 to determine the temperature-adjusted gas concentration values. The temperature compensation is obtained through a linear function with the factor (1+TC), which equals 1 at calibration (TC=0). In other words, the actual gas concentration is the measured gas concentration times the factor (1+TC). The factor TC is based on the formula $TC = a \times (T/Tc - 1)$, with a=temperature coefficient, T=ambient temperature and Tc=temperature at calibration.

The embodiment of the sensor shown in FIGS. 1–6 features measurement cells having relatively large volumes. As a result, the sensor of FIGS. 1–6 is suited for measurements in the low gas concentration range. A sensor having smaller volume measurement and compensation cells, and thus suitable for measurements in the high gas concentration range, is presented in FIGS. 8–13. While, as explained below, the sensor of FIGS. 8–13 differs in construction slightly from the sensor of FIGS. 1–6, the two sensors operate in the same fashion and the block diagram of FIG. 7 is applicable to both embodiments.

Figure 8:
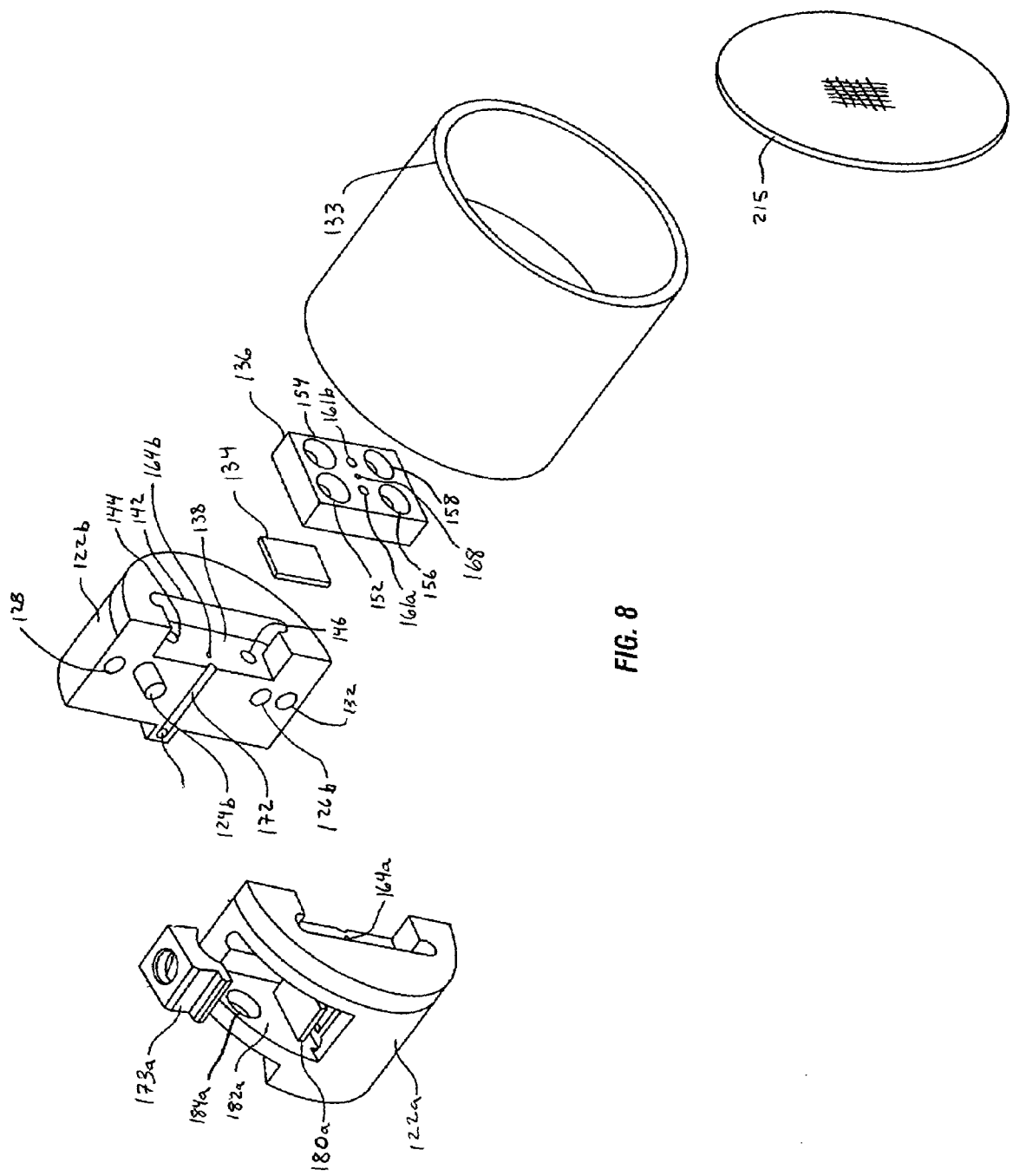
FIG. 8 is an exploded perspective view of another embodiment of the optoacoustic sensor of the present invention.

As with the embodiment illustrated in FIGS. 1–6, the embodiment of the optoacoustic gas sensor of the present invention illustrated in FIG. 8 features a cylindrical shape and contains two sensor body halves 122a and 122b. Furthermore, as with the embodiment of FIGS. 1–6, the body halves of FIG. 8 are joined with positioning or adjustment pins and positioning or adjustment bores (illustrated in FIG. 8 at 124b and 126b, respectively for body half 122b and not shown for body half 122a) and screws (not shown) that pass through holes 128 and 132 in body half 122b, and engage corresponding holes in body half 122a. Once assembled, the sensor body halves are encapsulated in a cover tube 133, acting as an additional holder of both sensor body halves. Circuit boards that are the same as those illustrated at 78 and 106 in FIGS. 1 and 7, and that feature the same components (microphones, lamps, etc.), are also positioned adjacent to the assembled body halves and within tube 133 in the manner described for FIG. 1.

As illustrated in FIG. 8, a membrane 134 is disposed under a perforated plate 136 that holds the membrane tight against the flat bottom 138 of a recess 142 formed in the top surface of the assembled sensor body by means of four screws (not shown) that engage holes 144 and 146 on body half 122b, corresponding holes on body half 122a, and holes 152, 154, 156 and 158 of plate 136.

The plate 136 preferably includes holes 161a and 161b that communicate with the gas drives 164a and 164b of body halves 122a and 122b, respectively. As in the embodiment of FIGS. 1–6, the gas drives connect the measurement/compensation cells of the sensor to the atmosphere. In the middle of the perforated plate 136, an additional bore 168 is set to connect the microphone compensation channel 172 of the assembled sensor body with the atmosphere.

Figure 10:
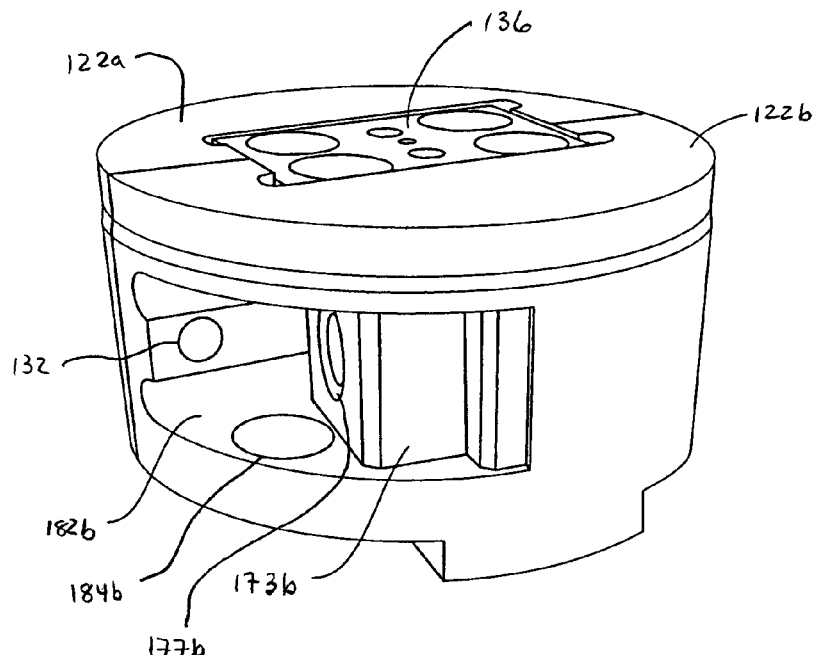
FIG. 10 is a perspective view of the assembled body halves, perforated plate and lamp holders of the sensor of FIGS. 8 and 9.
Figure 9:
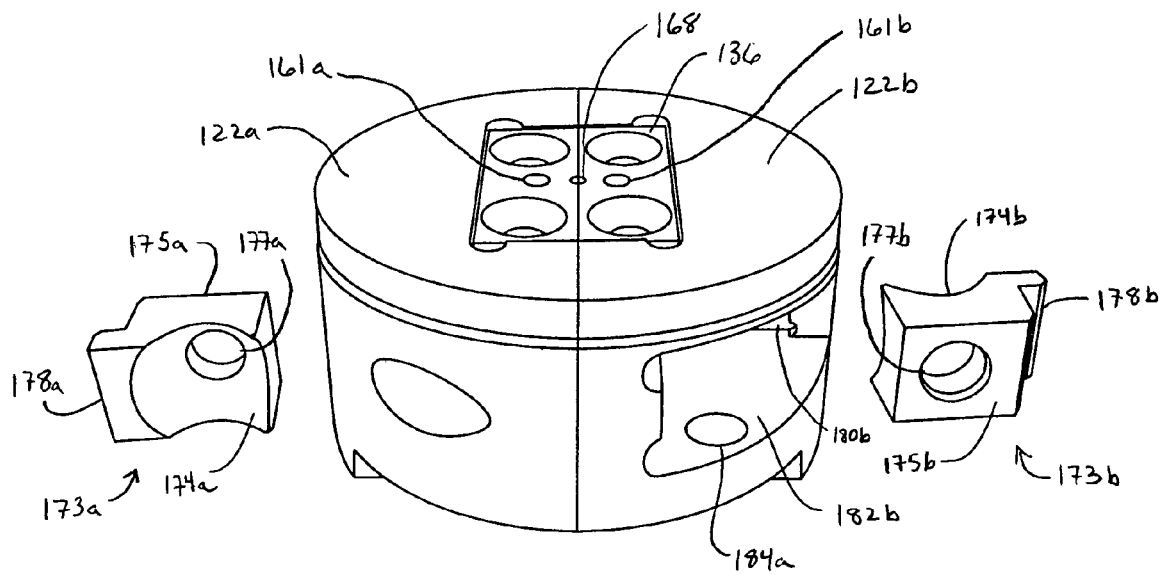
FIG. 9 is a perspective view of the assembled body halves and perforated plate and unassembled lamp holders of FIG. 8.

As illustrated in FIGS. 8–10, a pair of lamp holders 173a and 173b are positioned within a portion of lamp chambers 182a and 182b in body halves 122a and 122b, respectively. Each lamp holder, indicated in general at 173a and 173b in FIG. 9, features a hemispherical reflecting inner surface 174a and 174b, a flat outer surface 175a and 175b and an opening 177a and 177b. Each lamp holder also includes a ledge 178a and 178b that facilitates positioning each holder in lamp chambers 182a and 182b.

Figure 12:
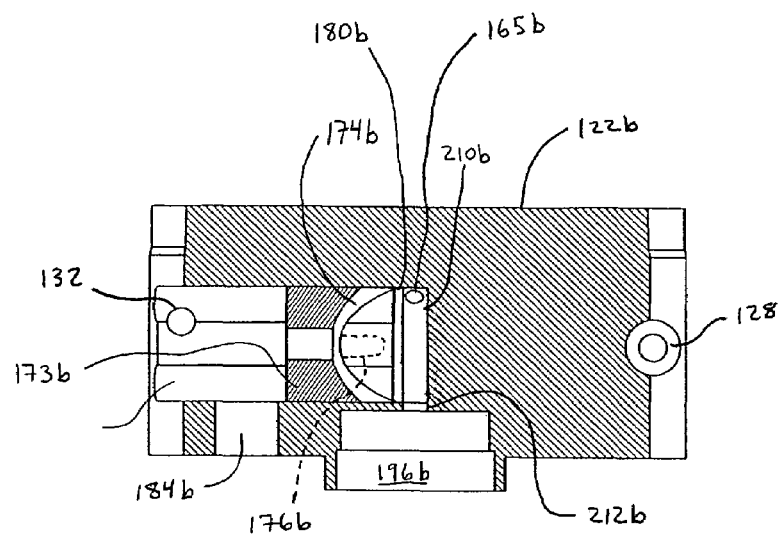
FIG. 12 is a sectional view of the sensor of FIG. 11 taken along line 12—12.
Figures 11, 13:
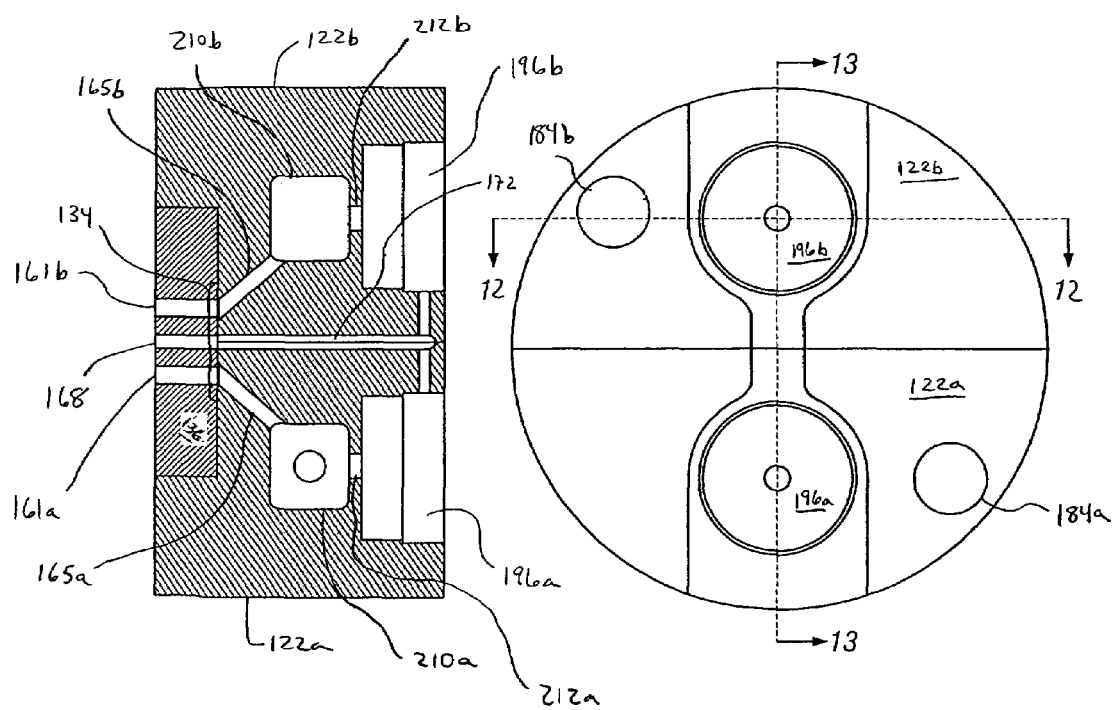
FIG. 11 is a bottom plan view of the assembled body halves of FIG. 9.
FIG. 13 is a sectional view of the sensor of FIG. 11 taken along line 13—13.

As illustrated in FIG. 8, a bandpass filter 180a (and 180b in FIG. 9) is positioned within the lamp chamber 182a (and 182b) prior to insertion of lamp holders 173a and 173b. When the lamp holders and bandpass filters are positioned within the lamp chambers, as illustrated in FIG. 10, gas measurement and compensation cells 210a and 210b, illustrated in FIGS. 12 and 13, are defined. The positioning of the reflecting inner surfaces 174a and 174b of lamp holders 173a and 173b enable a higher irradiation energy in each measurement and compensation cell 210a and 210b to be achieved. The bandpass filters 180a and 180b and the lamp holders 173a and 173b are preferably secured within lamp chambers 182a and 182b with adhesive. Tube 133 may also be used to help secure lamp holders 173a and 173b in position.

As illustrated in FIG. 8, each lamp chamber 182a and 182b is enclosed by sensor body tube 133. As described with regard to the embodiment of FIGS. 1–6, infrared lamps or light sources, one of which is illustrated in phantom at 176b in FIG. 12, that are mounted to a circuit board by flexible wires are inserted into the lamp chambers 182a (FIG. 8) and 182b (FIG. 2) through openings 184a and 184b, respectively, and then, after being rotated 90°, inserted into the lamp holders 173a and 173b through their respective openings 177a and 177b (FIG. 9).

As described with regard to the embodiment of FIGS. 1–6, a pair of microphones, which are also mounted to a circuit board and used for detecting pressure waves in the measurement and compensation cells 210a and 210b of the sensor, are mounted in microphone holding chambers, illustrated at 196a and 196b in FIGS. 11–12. A microphone compensation channel, illustrated at 172 in FIGS. 8 and 13, is formed by the assembled body halves 122a and 122b and terminates in a top opening that communicates with bore 168 of the perforated plate 136, shown in FIGS. 8–10. As illustrated in FIG. 13, the bottom end of the microphone compensation channel 172 communicates with the microphone holding chambers 196a and 196b. As a result, the undersides of the microphones are exposed to a pressure that is equal with the pressure of the ambient atmosphere. As illustrated in FIGS. 12 and 13, cells 210a and 210b communicate with microphone holding chambers 196a and 196b via acoustic passages 212a and 212b.

As illustrated in FIG. 13, cell 210a communicates with the ambient atmosphere through gas drive 165a, membrane 134 and hole 161a of plate 136. Similarly, as shown in FIGS. 12 and 13, cell 210b communicates with the ambient atmosphere through gas drive 165b, membrane 134 and hole 161b of perforated plate 136. The lower the target gas concentration range, the higher the volume of the measurement cell required, and the higher the number of gas drives required, and vice versa. Since the embodiment of FIGS. 8–13 is for measurements in the high gas concentration range, the number of gas drives provided is lower than for the embodiment of FIGS. 1–6 (where the lower gas concentration range is targeted). In both cases, the lengths of the gas drives are kept to the minimum to reduce dead volume and sensor response time The economic viability of a gas sensor has to take into account its manufacturability as well as its maintainability. In consideration of the sensor lifetime, anticipated to be at least ten years, the membrane used, typically a polytetrafluoroethylene (PTFE) membrane with non-woven polyester support, may have to be replaced in the course of regular maintenance to ensure a continuous tightness, a prerequisite to the functionality of the measurement cells. As described above, the sensor membrane (34 in FIGS. 1 and 134 in FIG. 8), equally allocated to both measurement cells, is made replaceable in the sensor of the present invention using a perforated plate (36 in FIGS. 1 and 136 in FIG. 8) holding the membrane to the sensor body by means of four screws. This feature has an important economic impact in that the cost of the membrane compared to the overall cost of the sensor is negligible and it may be easily replaced.

In order for the sensor to be used in classified and/or hazardous locations, that is, locations where there is a risk of explosion due to the likely presence (intermittent or continuous) of explosive gases (e.g. methane), the sensor must be designed according to the requirements of the National Electrical Code NEC 500. The most common and applied standards for gas sensors relate to either explosion-proof or intrinsically safe designs. The sensor of the present invention, including its evaluation circuit boards, can be designed either as explosion-proof or intrinsically safe so that the sensor may be installed in hazardous locations classified as Class I, Division 1, Groups ABCD, Temperature Class T6, the most stringent requirements for electrical equipment in classified locations.

The explosion-proof design is achieved in the sensor of the present invention by means of an optional sinter metallic disc, illustrated at 215 in FIG. 8, based on chrome nickel stainless steel with a porosity of 35 um, acting as flame arrestor, and being incorporated into the sensor housing rather than into the sensor body itself. More specifically, the flame arrestor 215 is positioned over the top end of the sensor so as to cover perforated plate 136 (or perforated plate 36 of FIG. 1). The flame arrestor, besides its primary function as flame arrestor, provides additional protection to the sensor membrane, and reduces the effects of pressure fluctuations and sudden pressure changes.

Without the flame arrestor 215 of FIG. 8, the sensor of the present invention may be designed as an intrinsically safe device (as an option), that is, one in which the sensor circuit in which any spark or any thermal effect produced in normal operation or specified fault conditions is not capable of causing an ignition of a given explosive gas atmosphere. Omission of the flame arrestor has the advantage that the unobstructed gas diffusion into the measurement cell through the membrane further reduces the sensor response time.

Finally, the sensor has been designed in two sensor body halves for a specific purpose. While the sensor body can be manufactured in one piece, encompassing all sensor elements and components, the concept of two separate body halves enables several different combinations of measurements cells for different gases, such as methane CH4 and carbon dioxide CO2. It is also possible to combine both measurement cells for a single gas one measurement cell for a low concentration range and the other for a high concentration range. In such a configuration, the sensor provides a much wider detection range with good resolution. If redundancy is the major requirement, two identical body halves can be combined to build a sensor for a single gas.

While the preferred embodiments of the invention have been shown and described, it will be apparent to those skilled in the art that changes and modifications may be made therein without departing from the spirit of the invention, the scope of which is defined by the appended claims.

What is claimed is:

1. An optoacoustic gas sensor comprising:
   a) a sensor body containing first and second measurement cells, said measurement cells in communication with the ambient atmosphere;
   b) first and second light sources in optical communication with said first and second measurement cells, respectively;

c) first and second microphones in communication with said first and second measurement cells, respectively; and d) evaluation and control electronics sequentially illuminating said first and second light sources so that one of said first and second measurement cells is gas active while the other cell is gas inactive so that the microphone in communication with the gas active cell generates a measurement signal due to optoacoustic pressure variations from a target gas present in the ambient atmosphere and the gas active cell.

2. The gas sensor of claim 1 wherein the microphone in communication with the gas inactive cell generates a compensation signal and said evaluation and control electronics subtracts the compensation signal from the measurement signal to provide an output signal.

3. The gas sensor of claim 1 wherein the sensor body includes first and second body halves, said first half containing the first measurement cell and said second half containing the first measurement cell.

4. The gas sensor of claim 3 wherein each of said sensor body halves features a pin or a bore that engages a corresponding pin or bore on the other sensor body half.

5. The gas sensor of claim 3 further comprising a cylindrical cover tube surrounding said first and second body halves.

6. The gas sensor of claim 1 further comprising a membrane in circuit between the ambient atmosphere and said first and second measurement cells.

7. The gas sensor of claim 1 wherein said first and second measurement cells communicate with the ambient atmosphere through gas drives.

8. The gas sensor of claim 7 wherein said sensor body includes a recess that communicates with the gas drives and further comprising a membrane and a perforated plate with the membrane positioned in the recess and sandwiched between the perforated plate and the sensor body.

9. The gas sensor of claim 8 wherein the perforated plate is removably secured to the sensor body by screws so that the membrane is replaceable.

10. The gas sensor of claim 1 wherein said sensor body also includes first and second microphone holding chambers holding the first and second microphones, respectively, and a microphone compensation channel in communication with the first and second microphone chambers and the ambient atmosphere so that a backside of each microphone is generally maintained at ambient atmosphere pressure.

11. The gas sensor of claim 1 further comprising an optical bandpass filter in circuit between at least one of said first and second light sources and said first and second measurement cells.

12. The gas sensor of claim 1 wherein said evaluation and control electronics includes a microprocessor in communication with the first and second microphones and the first and second light sources.

13. The gas sensor of claim 12 wherein the microprocessor continuously monitors the output signals of both microphones and, if the output signal of the microphone associated with the gas active measurement cell is not of equal or higher value than the output signal of the microphone associated with the gas inactive measurement cell, a signal is generated by the microprocessor indicating the fault.

14. The gas sensor of claim 1 wherein the second measurement cell, second light source and second microphone provide redundancy for the first measurement cell, first light source and first microphone.

15. The gas sensor of claim 1 wherein the first measurement cell and the second measurement cell feature differing volumes so that the gas sensor features an extended gas concentration measurement range.

16. The gas sensor of claim 1 wherein the evaluation and control electronics deliver a reading of the rate of increase of target gas concentration once a preset threshold concentration level is reached.

17. The gas sensor of claim 1 wherein the evaluation and control electronics gradually illuminate the light sources when they are sequentially illuminated to extend the lifetime of the light sources.

18. The gas sensor of claim 17 wherein the evaluation and control electronics deactivate the first microphone when the first light source is being gradually illuminated and wherein the evaluation and control electronics deactivate the second microphone when the second light source is being gradually illuminated.

19. An optoacoustic gas sensor for detecting at least one target gas present in the ambient atmosphere comprising:

a) a sensor body containing first and second measurement cells, said measurement cells in communication with the ambient atmosphere;

b) first and second light sources in optical communication with said first and second measurement cells, respectively;

c) first and second microphones in communication with said first and second measurement cells, respectively; and d) evaluation and control electronics in communication with said first and second lights sources and said first and second microphones, said evaluation and control electronics sequentially illuminating the first and second light sources so that a measurement signal due to optoacoustic pressure variations from the target gas is generated by the microphone of the illuminated cell and a compensation signal is generated by the microphone of the non-illuminated cell and said evaluation and control electronics subtracting the compensation signal from the measurement signal to provide an output signal.

20. The gas sensor of claim 19 wherein the sensor body includes first and second body halves, said first half containing the first measurement cell and said second half containing the first measurement cell.

21. The gas sensor of claim 20 further comprising a cylindrical cover tube surrounding said first and second body halves.

22. The gas sensor of claim 19 wherein said first and second measurement cells communicate with the ambient atmosphere through gas drives.

23. The gas sensor of claim 22 wherein said sensor body includes a recess that communicates with the gas drives and further comprising a membrane and a perforated plate with the membrane positioned in the recess and sandwiched between the perforated plate and the sensor body.

24. The gas sensor of claim 19 wherein said sensor body also includes first and second microphone holding chambers holding the first and second microphones, respectively, and a microphone compensation channel in communication with the first and second microphone chambers and the ambient atmosphere so that a backside of each microphone is generally maintained at ambient atmosphere pressure.

25. The gas sensor of claim 19 further comprising an optical bandpass filter in circuit between at least one of said first and second light sources and said first and second measurement cells.

26. The gas sensor of claim 19 wherein said evaluation and control electronics includes a microprocessor in communication with the first and second microphones and the first and second light sources.

* * * * *